United States Patent
Khan et al.

[11] Patent Number: 5,824,359
[45] Date of Patent: Oct. 20, 1998

[54] MEDICAL DEVICE LUBRICANT CONTAINING LECITHIN

[75] Inventors: Azhar J. Khan, West Valley; Mohammad A. Khan, Sandy, both of Utah

[73] Assignee: Becton Dickinson and Company, Franklin Lakes, N.J.

[21] Appl. No.: 884,780

[22] Filed: Jun. 30, 1997

[51] Int. Cl.$^6$ .............................. B05D 3/02; B05D 5/08; C07F 9/02
[52] U.S. Cl. .............................. 427/2.3; 426/72; 27/358; 27/370; 27/384; 554/80; 264/130; 264/322
[58] Field of Search .............................. 427/2.1, 2.3, 384, 427/387, 358, 370; 426/662, 72; 554/80; 508/107, 421; 264/130, 322

[56] References Cited

U.S. PATENT DOCUMENTS

| | | | |
|---|---|---|---|
| 4,661,300 | 4/1987 | Daugherty | 264/163 |
| 4,904,433 | 2/1990 | Williamitis | 264/130 |
| 4,938,960 | 7/1990 | Ismail | 424/195.1 |
| 5,063,090 | 11/1991 | Wannlund | 427/2.11 |
| 5,185,006 | 2/1993 | Williamitis | 264/131 |
| 5,266,359 | 11/1993 | Spielvogel | 427/2.1 |
| 5,282,850 | 2/1994 | Davidson | 427/2.24 |
| 5,496,581 | 3/1996 | Yianni et al. | 427/2.12 |
| 5,589,120 | 12/1996 | Khan et al. | 264/130 |
| 5,686,133 | 11/1997 | Amidon et al. | 427/2.22 |
| 5,688,747 | 11/1997 | Khan et al. | 508/208 |

OTHER PUBLICATIONS

"IGEPAL® Surfactants," GAF Corporation, 140 West 51 Street, New York, NY 10020, p. 10 (no date).
"TETRONIC® Block Copolymer Surfactants," BASF Wyandotte Corporation, 100 Cherry Hill Road, Parsippany, NJ 07054, pp. 8–9 (no date).
Material Safety Data Sheet for: MASIL® 29, Silicone Surfactant, by PPG® Industries, Inc., Specialty Chemicals, 3938 Porett Drive, Gurnee, IL 60031, pp. 1–3 (Feb. 1995).
Material Safety Data Sheet for: MASIL® 1066, C, Silicone Glycol, by PPG® Industries, Inc., Specialty Chemicals, 3938 Porett Drive, Gurnee, IL 60031, pp. 1–3 (Feb. 1995).
Material Safety Data Sheet for: MASIL® 280, Silicone Glycol, by PPG® Industries, Inc., Specialty Chemicals, 3938 Porett Drive, Gurnee, IL 60031, pp. 1–3 (Feb. 1995).

*Primary Examiner*—Diana Dudash
*Attorney, Agent, or Firm*—Eric M. Lee

[57] ABSTRACT

The lubricant of this invention is lecithin. The lubricant is applied to the surface to be lubricated by forming a colloidal solution of water and lecithin. This solution may also include a surfactant, Vitamin E or its derivative. In addition, a solution stabilizer and an antimicrobial agent may be used to clarify the solution and to inhibit microbial growth in the solution.

19 Claims, 1 Drawing Sheet

MEDICAL DEVICE LUBRICANT CONTAINING LECITHIN

BACKGROUND OF THE INVENTION

This invention relates in general to a lubricant used during the manufacture of intravenous (IV) catheters. In addition, this invention relates to a lubricant solution that facilitates application of the lubricant to a surface and that uses water as the carrier or solvent.

IV catheters are designed to infuse normal intravenous solutions, including antibiotics and other drugs, into a patient. These catheters are also used to withdraw blood from the patient for normal blood-gas analysis as well as other blood work.

The typical catheter is hollow and is extruded out of suitable plastic material such as Teflon, polyvinyl chloride, polyethylene, polyurethane or polyether urethane. In order to insert a catheter into a patient, an introducer needle is used. The needle is typically formed from stainless steel and is hollow. Its distal tip is ground to a sharp tip for easy insertion into the patient. The catheter is initially located coaxially around the introducer needle in an "over the needle" arrangement. The internal diameter of the catheter tip is slightly less than the outer diameter of the needle so that the catheter tip has an interference fit on the needle. The interference fit is necessary so that when the catheter and introducer needle assembly is taken out of the package, the catheter remains snugly on the needle and does not easily slip off. This interference fit also facilitates insertion of the catheter and introducer needle assembly into the patient's vein because it minimizes the chance that the catheter tip will fold over or peel back on the needle tip.

Placement of the catheter and introducer needle assembly into the patient causes sharp pain to the patient. In order to facilitate insertion of the assembly into the vein and to minimize patient discomfort, the shape of the catheter tip is formed so as to produce minimal trauma to the patient during insertion of the catheter into the patient and while the catheter is in place in the patient. Such a preferred tip shape that provides these characteristics has a tapered outer wall and an angled tip and is disclosed in U.S. Pat. No. 4,588,398. A process for making that catheter tip, known as the tipping process, is disclosed in U.S. Pat. No. 4,661,300. In this tipping process, the catheter blank is placed on a mandrel. A die having an interior molding surface, which is tapered according to the tip desired on the catheter, is aligned axially with the mandrel. The tip of the catheter blank is heated, typically using RF energy, so that it is flowable. The mandrel and die are brought together so the distal edge of the mandrel engages the tapered portion of the die. This action cleanly forms a smooth and uniform tapered tip for the catheter.

After the catheter is tipped, it must be free of defects such as incomplete formation, substantial flash or jagged edges. The tip must also look smooth and be free of roll-overs. In addition, the length of the catheter must remain within a desired specification after the tipping process. Visual or microscopic examination may be used to determine if there are any tip defects and if the length of the catheter is within specifications. Typically a lubricant is used to allow the tipped catheter to be easily removed from the mandrel and die. If a lubricant is not used, the tipped catheter could stick to the mandrel or die resulting in a deformed catheter when it is removed from the mandrel or die.

Standard tipping lubricants include polydimethyl siloxanes such as Dow Corning DC 360 or curable silicones such as Dow Corning 44159 MDX which are amine terminated and moisture curable. Non-curable amine terminated polydimethyl siloxanes have also been used for this purpose. Such lubricants are described in, for example, U.S. Pat. Nos. 3,574,673; 4,664,657; 4,904,433; and 5,185,006.

An additional mechanism that is used to facilitate insertion of the catheter and introducer needle assembly into the patient is lubrication. Typically the catheter will be lubricated to minimize drag between the catheter and the patient's skin. In addition, lubricant can be applied to the needle to minimize adhesion between the catheter and the needle to facilitate removal of the needle from the catheter. Such catheter and needle lubricants include the same type of lubricants that have heretofore been used during the tipping process.

The amount of lubricant needed to provide lubricity to the catheter, between the catheter and the needle and between the catheter blank and the mandrel and die during the tipping process is very small. Thus in order to control the application of the lubricant, the surface to be lubricated is coated with a lubricant solution that contains the lubricant and a carrier or solvent. Use of a lubricant solution also facilitates application of the lubricant to the inside surface as well as outside surface of the catheter. After the lubricant solution is applied to the surface, the carrier or solvent evaporates leaving the lubricant behind the surface. The silicone oils used as typical lubricants are hydrophobic. Therefore, these compounds must be dissolved in organic solvents in order to prepare a lubricant solution which can be applied to the surface to be lubricated before the tipping process can begin. The primary solvent that has been used heretofore is freon because it is nonflammable and evaporates quickly. Unfortunately, because of recent concerns that chlorofluorocarbons (CFC) react with and destroy the earth's protective ozone layer, the production and use of CFC will cease in the near future. Thus other solvents must be used. Other organic solvents, such as alcohols and hydrocarbons, are highly flammable. Thus, it is too dangerous to use large amounts of these solvents in the tipping process.

SUMMARY OF THE INVENTION

It is therefore an object of this invention to provide a lubricant that does not require the use of a CFC as the solvent or the carrier.

It is another object of this invention to provide a lubricant solution that is "environmentally friendly".

It is still another object of this invention to provide a lubricant solution that is not flammable.

The lubricant of this invention is lecithin. The lecithin may also be combined with a silicone surfactant. Preferably silicone surfactants are used but other surfactants can also be used. Since lecithin can be dispersed in water and surfactants are water soluble, water is used as the carrier to form the lubricant solution. The combination of lecithin and water forms a colloidal solution which is placed on the surfaces to be lubricated by dipping, brushing or spraying. Upon evaporation of the water, the lecithin and surfactant, if included in the solution, remain behind to provide lubricity. The tipping process of this invention requires that the tip portion of the catheter blank be dipped in the colloidal solution or to otherwise have this colloidal solution applied to the surfaces to be lubricated such as by brushing or spraying the colloidal solution onto such surfaces. Once the water evaporates, the catheter blank is mounted on a mandrel and heated. A die and the mandrel are brought into engagement to form the catheter tip. The tipped catheter is then easily and quickly removed from the die and the mandrel.

The above and other objects and advantages of the invention will be apparent upon consideration of the following detailed description.

BRIEF DESCRIPTION OF THE DRAWINGS

The preferred embodiments are illustrated in the drawings in which like reference numerals refer to like elements and in which.

DETAILED DESCRIPTION OF THE INVENTION

Figure 1:
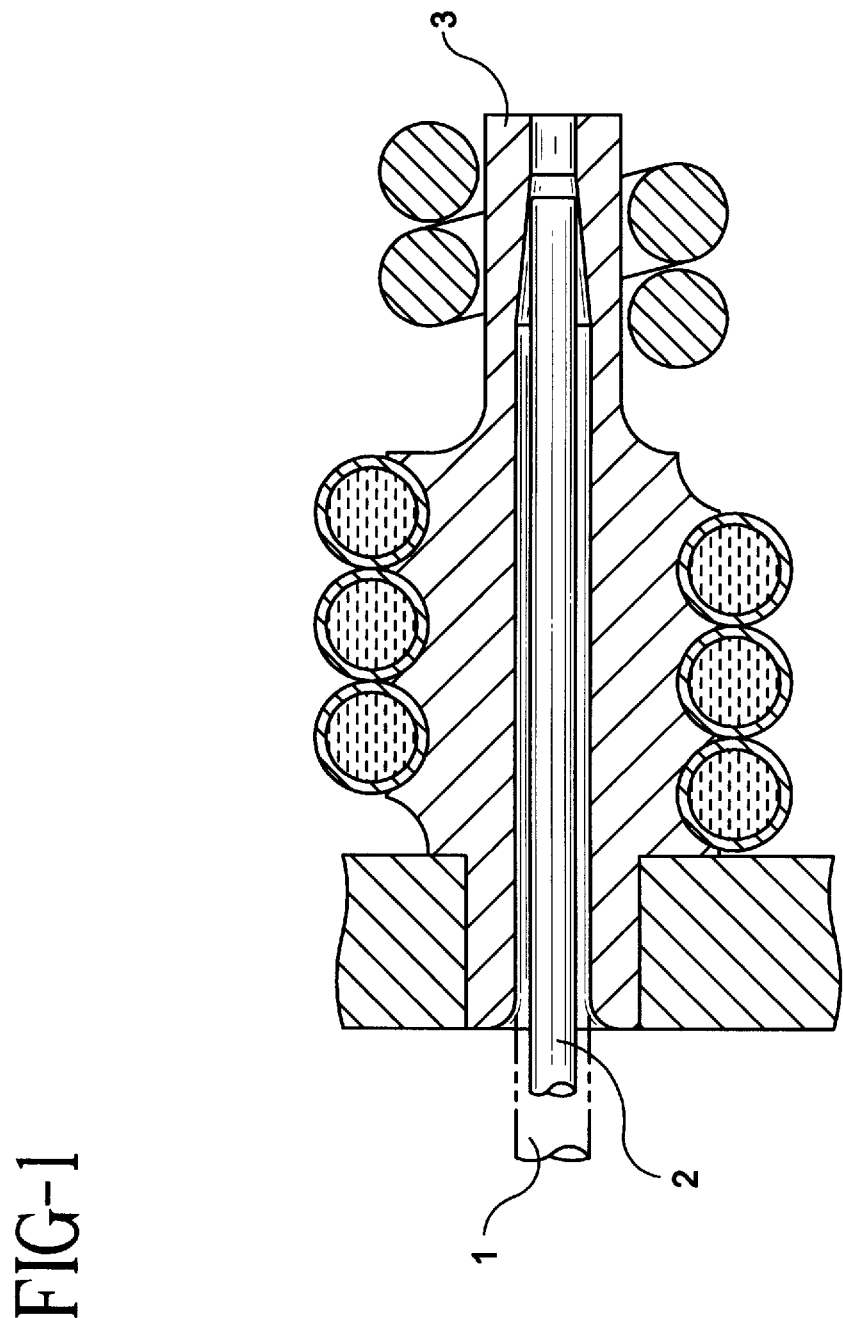
FIG. 1 is a cross-sectional view of a portion of a die and mandrel arrangement with a catheter blank thereon with the mandrel engaged with the die to form the catheter tip.

Although this invention is described in terms of its application to the tipping of IV catheters, it is to be understood that this invention could be used on various medical devices and in processes where a lubricious surface is desirable. For example, this invention can be used to lubricate a catheter and introducer needle to facilitate insertion thereof into a patient.

The lubricant of this invention is lecithin, chemically known as phosphotidylcholine. The chemical structure of lecithin is given below:

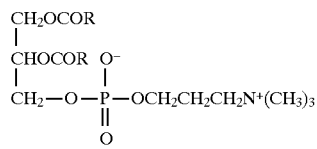

Preferably between about 0.5% and about 10.0% by weight of lecithin is used in the lubricant solution. Since lecithin can be dispersed in water, the lubricant solution includes lecithin and water. This solution can also include other ingredients such as surfactants, vitamin E, a solution stabilizer and an antimicrobial agent.

Surfactants are water soluble, emulsifiers and are good lubricating fluids. The surfactant should comprise between about 1.0% and about 10.0% by weight of the lubricant solution. Preferably, the surfactant that is used is a silicone glycol sold under the Masil® trademark by PPG Industries, Inc. However, other silicone surfactants such as polyalkylene oxide-modified polydimethylsiloxane block copolymers sold under the Silwet® trademark by OSI Specialties, Inc., block copolymer surfactants sold under the Tetronic® trademark by BASF Wyandotte Corporation, and ethoxylated alkylphenol surfactants sold under the IGEPAL® trademark by GAF Corporation may also be used.

Vitamin E is chemically known as alpha-tocopherol and is an antioxidant. Since vitamin E is an antioxidant it prevents degradation of the lubricant solution through oxidation and thus minimizes the effects of aging. In addition, vitamin E and its derivatives, including vitamin E acetate and vitamin E succinate, enhance the lubricity of the lubricant of this invention. Preferably between 0.1% and 1% by weight of vitamin E or its derivatives is used. The molecular structure of vitamin E is shown below:

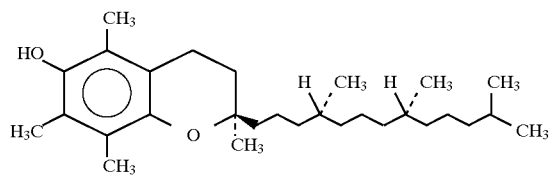

Cosmocil, chemically known as polyhexamethylene biguanide hydrochloride, is an excellent solution stabilizer and antimicrobial agent which inhibits microbial growth in the water based lubricant solution or on the coated surface of the device. Preferably between about 1% and about 5% by weight of cosmocil is used. Another solution stabilizer that can be used is a quaternary ammonium salt. When this is used anti-microbial agents should be included. Examples of anti-microbial agents are: iodophors; phenols; phenolic compounds such as parachloro-meta-xylenol; and other biguanides such as chlorhexidine gluconate. Even where cosmocil is used, these anti-microbial agents may still be used in the solution. However, cosmocil is preferably used alone because it is less toxic than the other anti-microbial agents. Its molecular structure is shown below:

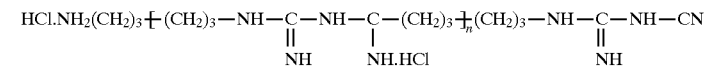

After the lubricant solution is applied to the surface to be lubricated, i.e. the catheter blank, the catheter blank 1 to be tipped is mounted onto a mandrel 2 supported on a carriage (not shown). A die 3 having an interior molding surface, with at least one portion of which is tapered according to the tip desired on the finished catheter, is aligned axially with the mandrel 2. The carriage is moved toward the die 3 such that the end of the catheter blank 1 to be tipped engages the interior molding surface. The carriage is halted at a point after the catheter blank 1 has engaged the tapered portions of the interior molding surface of the die 3, and is biased toward the die 3 with only sufficient force to cause the catheter blank 1 to move further into the die as the catheter blank 1 is heated by RF energy to its melting point and begins to flow. See FIG. 1. The catheter blank 1 is then allowed to heat in the die 3 and is moved into the die 3 as it begins to melt and flow under the biasing force. The mandrel 2 is positioned so that its distal corner is against the tapered portion of the die 3, thus cleanly forming the leading edge of the catheter. The die 3 and catheter therein are then cooled, and the carriage is reversed such that the catheter may be withdrawn from the die 3. Finally, the catheter is removed from the mandrel 2. There is no flash left on the leading edge because of the contact between mandrel 2 and die 3.

Example No. 1

As a control, 20 gauge and 18 gauge commercial Insyte® catheters were tested for tip adhesion to an introducer needle and penetration through dental dam having a 13.0 mil±0.5 mil thickness. The lubricants used were as follows:

Needle lubricant—3.0% solution of 1 MM CSTK polydimethylsiloxane in HCFC

Catheter lubricant—2.5% solution of 12,500 CSTK polydimethylsiloxane in HCFC

Catheter tipping lubricant—0.65% solution 2000 CSTK propylamino terminated polydimethylsiloxane in HCFC Test results are reported in the following table:

| Test | 20 Gauge Insyte ® | 18 Gauge Insyte ® |
|---|---|---|
| Tip Adhesion (g) | 86 (12) | 133.9 (45) |
| Needle Tip (g) | 15.9 (1.3) | 16.4 (1.3) |
| Catheter Tip (g) | 12.2 (0.7) | 13.6 (0.7) |
| Catheter Drag (g) | 2.9 (0.3) | 3.9 (9.5) |

Sample Size = 10
( ) = standard deviation.

Catheter tips formed using the above catheter tipping lubricant generally are Grade 3 tips. As identified below, a grade 3 tip is acceptable, does not stick to the mandrel or die and has no feathering.

In comparison, a colloidal lubricant solution was prepared by stirring a known amount of soybean lecithin in water with a magnetic stirrer. This colloidal lubricant solution was used to coat a catheter blank to be tipped. Twenty gauge Insyte® catheters were used in these studies.

| Ingredients | Composition #1 % By Weight | Composition #2 % By Weight | Composition #3 % By Weight |
|---|---|---|---|
| Lecithin | 1 | 2 | 5 |
| Water | 99 | 98 | 95 |

These solutions were used in the catheter tipping process. Thirty catheter tips were formed and the catheter tip was rated as follows:

Grade 1: Tip sticking to the mandrel, tip feathering

Grade 2: Tip not sticking to the mandrel but feathering

Grade 3: Tip acceptable, does not stick and has no feathering

Grade 4: Tip well rounded, smooth, and free from any defects

Composition #1 produced a catheter tip quality of Grade 1.

Composition #2 produced a catheter tip quality of Grade 3.

Composition #3 produced a catheter tip quality of Grade 4.

From the above results, it is clear that lecithin alone with a concentration in excess of 1% by weight of the lubricant solution works as a tipping lubricant. However, as increasing amounts of lecithin are used the solution becomes increasingly viscous and difficult to work with.

After tipping, these catheters and associated introducer needles were dipped into the above colloidal lubricant solutions and then assembled. The tip adhesion was tested and the assemblies were penetrated through a natural latex membrane, 13.0 mil±0.5 mil in thickness. The results are reproduced below:

| Test | Composition #1 | Composition #2 | Composition #3 |
|---|---|---|---|
| Tip Adhesion (g) | 125.2 (52.6) | 202.3 (68.7) | 375.4 (150.2) |
| Needle Tip (g) | 32.2 (5.8) | 26.8 (5.6) | 29.9 (8.7) |
| Catheter Tip (g) | 36.3 (6.4) | 39.2 (7.1) | 42.5 (7.5) |
| Catheter Drag (g) | 14.4 (3.8) | 19.7 (6.0) | 14.6 (1.4) |

Sample Size = 10
( ) = standard deviation

As is apparent, these values are slightly higher than those of currently marketed products lubricated with dimethylsiloxane fluids. Thus, the use of lecithin alone works well as a tipping lubricant but could be improved when used as a needle lubricant or a catheter lubricant.

Example No. 2

Lecithin was tested in combination with a silicone surfactant as a tipping lubricant. The following formulations were prepared and the lubricant solutions were used to coat a catheter blank prior to the tipping process. Some of the lubricant solutions were also used to assess the lubricating properties of the lecithin and silicone surfactant as a needle lubricant and a catheter lubricant.

| | Composition, Percent W/W | | | | | | |
|---|---|---|---|---|---|---|---|
| Ingredients | 1 | 2 | 3 | 4 | 5 | 6 | 7 |
| Lecithin | 1.03 | 0.64 | 1.07 | 0.61 | 1.01 | 1.03 | 1.0 |
| Silicone Surfactant (Masil 1066C) | — | — | — | 2.07 | 2.8 | 3.5 | — |
| Silicone Surfactant (Masil 29) | 2.0 | 3.5 | 3.5 | — | — | — | — |
| Igepal CA-720 | — | — | — | — | — | — | 1.0 |
| Water | 96.97 | 95.86 | 95.43 | 97.32 | 96.19 | 95.44 | 98.00 |
| Tip Quality Grade | 1 | 3 | 4 | 2 | 4 | 4 | 1 |

Sample Size = 30

As evident from the data above, lecithin in combination with a silicone surfactant also works as a tipping lubricant. The addition of a surfactant provides additional lubricity and improves emulsification of the lecithin.

Composition #3, #6 and #7 were also tested to assess the lubrication properties of the lecithin and silicone surfactant as a catheter lubricant and as a needle lubricant. All experiments were done using 20 gauge Insyte® catheters. The results of the tip adhesion studies and penetration tests through latex having a 13.0 mil±0.5 mil thickness are presented below:

| Test | Composition #3 | Composition #6 | Composition #7 |
|---|---|---|---|
| Tip Adhesion (g) | 73.7 (21.7) | 72.3 (24.1) | 125.5 (29.5) |
| Needle Tip (g) | 22.1 (2.3) | 20.9 (2.6) | 23.7 (5.5) |
| Catheter Tip (g) | 19.9 (2.9) | 20.2 (2.3) | 26.8 (4.5) |
| Catheter Drag (g) | 6.4 (0.7) | 6.2 (0.9) | 10.4 (2.6) |

Sample Size = 10
( ) = standard deviation

These values are comparable to those currently marketed products that are lubricated with dimethylsiloxane fluids.

Example No. 3

Various compositions were evaluated where differing amounts of lecithin and a surfactant were used. These compositions were used in the catheter tipping process. Thirty catheter tips were formed and the catheter tips were rated as before for each composition.

| Composition No. | Silicone Surfactant (Masil 29)(% by weight) | Lecithin (% by weight) | Rating |
| --- | --- | --- | --- |
| 1 | 2.75 | 10.00 | 4 |
| 2 | 2.75 | 5.25 | 4 |
| 3 | 3.50 | 0.50 | 2 |
| 4 | 2.00 | 5.25 | 4 |
| 5 | 2.00 | 0.50 | 2 |
| 6 | 2.00 | 10.00 | 4 |
| 7 | 3.50 | 5.25 | 4 |
| 8 | 2.75 | 0.50 | 2 |
| 9 | 3.50 | 10.00 | 4 |

| Composition No. | Surfactant (Igepal CA760) (% by weight) | Lecithin (% by weight) | Rating |
| --- | --- | --- | --- |
| 10 | 2.00 | 10.00 | 4 |
| 11 | 2.75 | 5.25 | 4 |
| 12 | 2.00 | 0.50 | 2 |
| 13 | 3.50 | 0.50 | 2 |
| 14 | 2.75 | 10.00 | 4 |
| 15 | 3.50 | 5.25 | 4 |
| 16 | 2.00 | 5.25 | 4 |
| 17 | 2.75 | 0.50 | 2 |
| 18 | 2.50 | 10.00 | 4 |

These values indicate that use of about 2% by weight of a surfactant in combination with between about 5% by weight and 10% by weight of lecithin works as a tipping lubricant.

Example No. 4

Several compositions utilizing silicone surfactants, Vitamin E and a solution stabilizer were prepared and used in the tipping process. The same solutions were used for needle lubrication and catheter lubrication. In this study, 18 gauge Insyte® catheters were used. The composition of the solutions and tipping characteristics are given in the following table:

| Ingredients | Composition, % By Weight | | | |
| --- | --- | --- | --- | --- |
|  | 1 | 2 | 3 | 4 |
| Silicone Surfactant (Masil 29) | 5.8 | — | — | — |
| Silicone Surfactant (Masil 1066C) | — | 5.03 | — | 4.0 |
| Silicone Surfactant (Masil 280) | — | — | 5.02 | — |
| Vitamin E | 0.28 | 0.28 | 0.27 | 0.25 |
| Cosmocil | 50 ppm | 50 ppm | 50 ppm | — |
| Tetronic 904 | — | — | — | 1.5 |
| Water (QSTO) | 100 | 100 | 100 | 100 |
| Tip Quality Grade | All Sticks | All Sticks | All Sticks | All Sticks |

Sample Size = 30

As can be seen, none of the solutions described in Example #3 were suitable for tipping of the catheters in the tipping process. These silicone surfactants, therefore, cannot be used in the tipping process. However, when lecithin is present in the lubricant solution with these silicone surfactants, tipping can be achieved. And, as has been demonstrated in Example #2, these silicone surfactants may also enhance the lubrication characteristics of lecithin for use as a catheter lubricant and as a needle lubricant.

The tip adhesion data and the penetration test data through latex dental dam having a 13.0 mil±0.5 mil thickness are reproduced below:

| Test | 1 | 2 | 3 | 4 |
| --- | --- | --- | --- | --- |
| Tip Adhesion (g) | 185.9 (23.4) | 234.1 (23.4) | 254.6 (25.2) | 268.7 (31.5) |
| Needle Tip (g) | 20.8 (4.0) | 22.9 (4.2) | 22.7 (2.4) | 22.0 (3.2) |
| Catheter Tip (g) | 14.2 (1.1) | 13.1 (0.9) | 15.4 (1.1) | 14.3 (1.3) |
| Catheter Drag (g) | 5.9 (1.0) | 4.1 (0.5) | 7.4 (1.2) | 6.6 (0.4) |

Sample Size = 10
( ) = standard deviation

It can be seen that these silicone surfactants possess lubrication properties for the introducer needle and catheter body.

Thus, it is seen that a new tipping lubricant is provided that does not require the use of CFC as a solvent and is thus "environmentally friendly." The lubricant solution is also nonflammable.

We claim:

1. A method for forming a shaped tip on a catheter comprising:
   applying lecithin to a a portion of an untipped catheter tubing that is to be tipped;
   placing the untipped catheter tubing on a mandrel;
   heating the untipped catheter tubing to soften the portion of the untipped catheter tubing that is to be tipped;
   engaging the mandrel with a die to form the catheter tip; and
   removing the shaped catheter tubing from the die and mandrel.

2. The method of claim 1 wherein the lecithin is applied to a portion of an untipped catheter tubing that is to be tipped by applying a lubricant solution of lecithin and water to the portion of the untipped catheter tubing that is to be tipped.

3. The method of claim 2 wherein the lecithin comprises between about 0.5% and about 10% by weight of the solution.

4. The method of claim 2 wherein the lubricant solution also includes a separate surfactant.

5. The method of claim 4 wherein the surfactant comprises between about 1% and about 10% by weight of the solution.

6. The method of claim 4 wherein the lubricant solution also includes vitamin E, vitamin E acetate or vitamin E succinate.

7. The method of claim 6 wherein the lubricant solution also includes a solution stabilizer.

8. The method of claim 7 wherein the solution stabilizer is selected from the group consisting of a quaternary ammonium salt or polyhexamethylene biguanide hydrochloride.

9. The method of claim 7 wherein the lubricant solution also includes an anti-microbial agent.

10. A lubricant consisting essentially of lecithin and a silicone surfactant.

11. A lubricant consisting essentially of lecithin, a silicone surfactant and vitamin E, vitamin E acetate or vitamin E succinate.

12. A method for lubricating a medical device, comprising:
    applying a solution of lecithin and water to the medical device; and
    evaporating the water.

13. The method of claim 12 wherein the lecithin comprises between about 0.05% and about 10% by weight of the solution.

14. The method of claim 12 wherein the solution also comprises a separate surfactant.

15. The method of claim 14 wherein the surfactant comprises between about 1% and about 10% by weight of the solution.

16. The method of claim 14 wherein the solution also comprises vitamin E, vitamin E acetate or vitamin E succinate.

17. The method of claim 16 wherein the solution also comprises a solution stabilizer.

18. The method of claim 17 wherein the solution stabilizer is selected from the group consisting of a quaternary ammonium salt or polyhexamethylene biguanide hydrochloride.

19. The method of claim 17 wherein the solution also comprises an antimicrobial agent.

* * * * *